United States Patent
McCarty

(10) Patent No.: US 9,717,515 B1
(45) Date of Patent: Aug. 1, 2017

(54) MEDICAL DEVICE FOR SLEEVE GASTRECTOMY SURGERY

(71) Applicant: Todd McCarty, Dallas, TX (US)

(72) Inventor: Todd McCarty, Dallas, TX (US)

(73) Assignee: MW Support Services, LLC, Dallas, TX (US)

(*) Notice: Subject to any disclaimer, the term of this patent is extended or adjusted under 35 U.S.C. 154(b) by 0 days.

(21) Appl. No.: 14/822,638

(22) Filed: Aug. 10, 2015

(51) Int. Cl.
*A61B 17/24* (2006.01)
*A61B 17/221* (2006.01)
*A61B 17/00* (2006.01)
*A61F 5/00* (2006.01)

(52) U.S. Cl.
CPC ...... *A61B 17/221* (2013.01); *A61B 17/00234* (2013.01); *A61B 2017/003* (2013.01); *A61B 2017/00278* (2013.01); *A61B 2017/00358* (2013.01); *A61B 2017/00818* (2013.01); *A61B 2017/2212* (2013.01); *A61F 5/0083* (2013.01)

(58) Field of Classification Search
CPC .......... A61B 17/32056; A61B 17/221
See application file for complete search history.

(56) References Cited

U.S. PATENT DOCUMENTS

| | | | |
|---|---|---|---|
| 3,955,578 A | 5/1976 | Chamness et al. | |
| 5,647,372 A | 7/1997 | Tovey et al. | |
| 5,766,202 A * | 6/1998 | Jones | A61M 29/00 604/270 |
| 6,406,440 B1 | 6/2002 | Stefanchik | |
| 8,142,347 B2 * | 3/2012 | Griego | A61B 17/32056 600/110 |
| 8,172,772 B2 * | 5/2012 | Zwolinski | A61B 10/06 600/562 |

(Continued)

OTHER PUBLICATIONS

Mintz Y, Horgan S, Savu MK, et al. Hybrid natural orifice translumenal surgery (NOTES) sleeve gastrectomy: a feasibility study using an animal model. Surg Endosc. 2008;22:1798.

(Continued)

*Primary Examiner* — Eric Rosen
*Assistant Examiner* — Son Dang
(74) *Attorney, Agent, or Firm* — Law Office of Sam Sokhansanj PLLC

(57) ABSTRACT

A dual-purpose surgical bougie is disclosed for vertical sleeve gastrectomy (VSG) procedures, and other related operations, that can serve the purpose of both operating as a guide or dilator for stapling and resecting a stomach and also securing, containing, and trans-orally extracting the resected stomach, thereby promoting faster patient recovery, minimizing and reducing the size and number of incisions, and further minimizing VSG procedure related complications, among other advantages. In one aspect of the disclosure described herein, the dual-purpose medical device can include a surgical bougie having a distal end and a proximal end, wherein the bougie can be made of at least one of rubber, silicone, plastic, and metal. In addition, the bougie can include a channel or passage disposed within its central axis extending from its distal end to the proximal end, and a securement member coupled to the bougie. Here, the securement member can extend from the distal end of the flexible member, such that the securement member securely couples to a resected body tissue thereby allowing the bougie to trans-orally extract the resected body tissue.

16 Claims, 10 Drawing Sheets

(56) References Cited

U.S. PATENT DOCUMENTS

| 8,403,838 B2 | 3/2013 | Roth et al. |
| 8,454,503 B2 | 6/2013 | Roth et al. |
| 8,920,305 B2 | 12/2014 | Jacobs et al. |
| 2002/0143346 A1 | 10/2002 | McGuckin, Jr. et al. |
| 2005/0251158 A1 | 11/2005 | Saadat et al. |
| 2008/0312559 A1 | 12/2008 | Santilli et al. |
| 2011/0288576 A1 | 11/2011 | Hoffman |
| 2012/0016393 A1 | 1/2012 | Murray et al. |
| 2012/0123463 A1 | 5/2012 | Jacobs |
| 2013/0178698 A1 | 7/2013 | Bender et al. |
| 2014/0073858 A1 | 3/2014 | Sherwinter |
| 2014/0107698 A1 | 4/2014 | Inge |

OTHER PUBLICATIONS

Non Final Office Action received for U.S. Appl. No. 15/581,586, dated Jun. 1, 2017, 47 pages.

"Maloney & Hurst Bougie for Esophageal Dilation," Rusch, publication date unknown, one page.

* cited by examiner

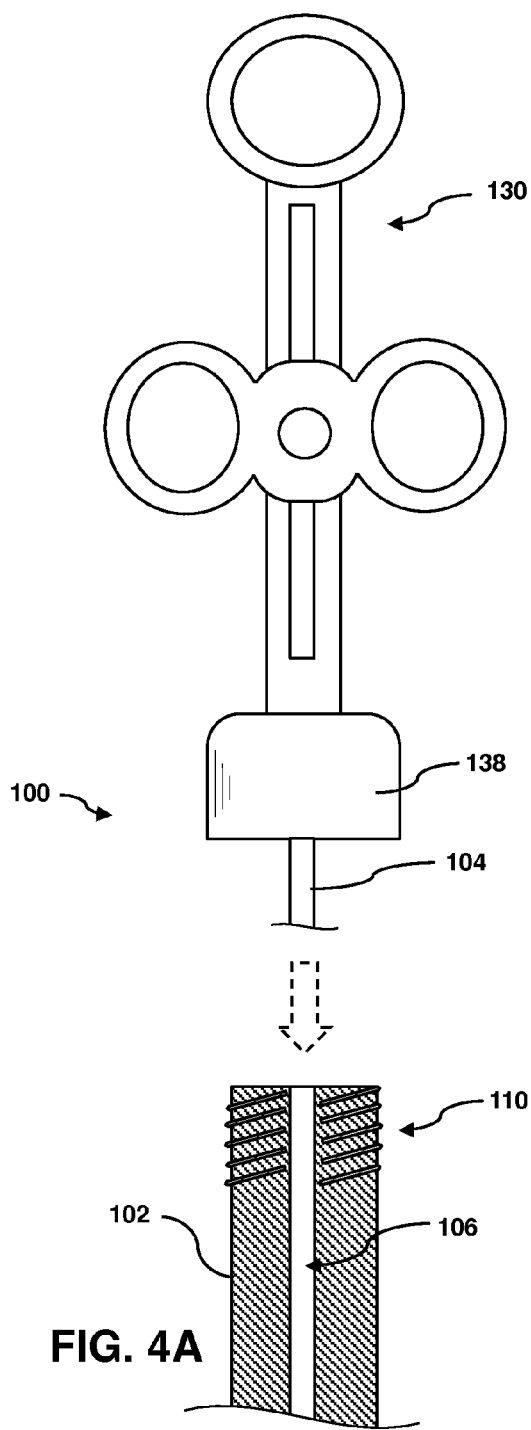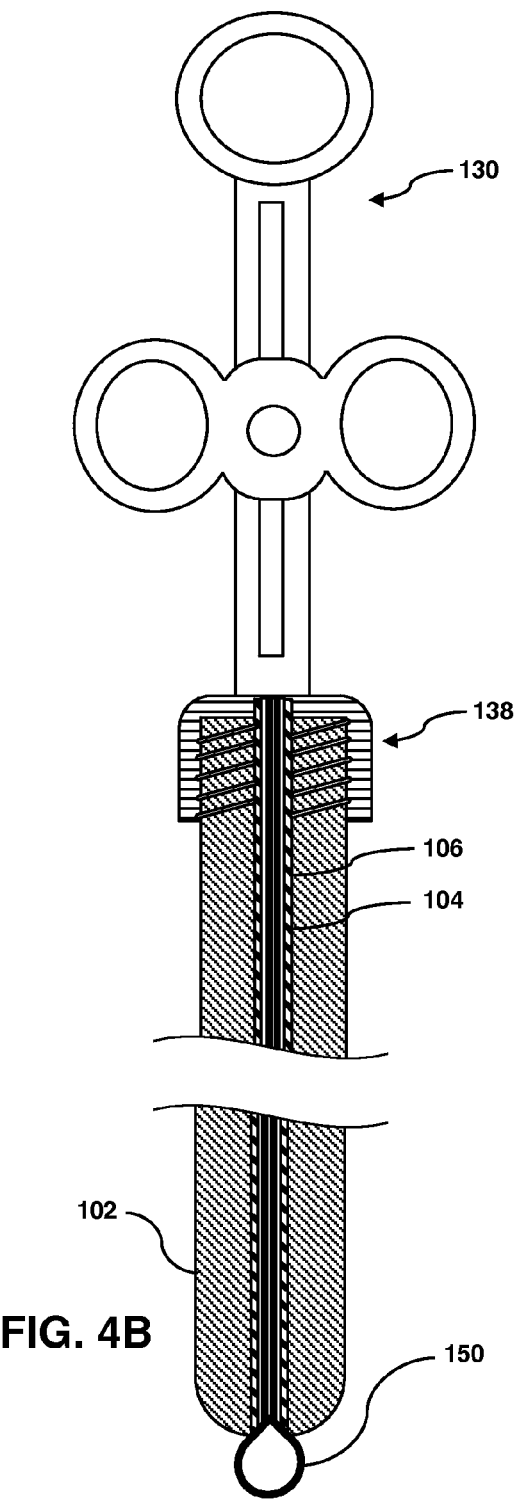
FIG. 4A
FIG. 4B

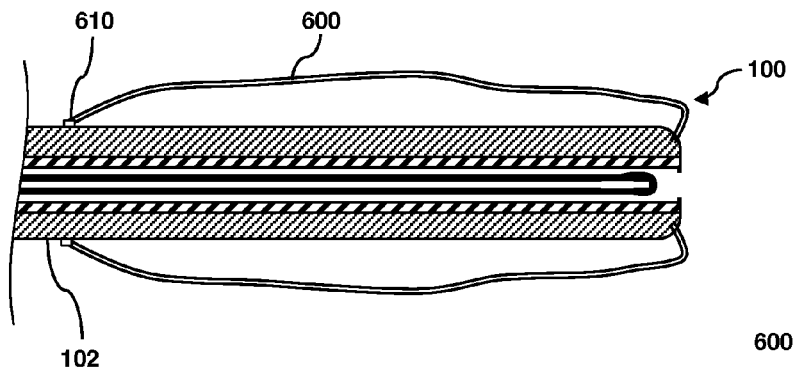
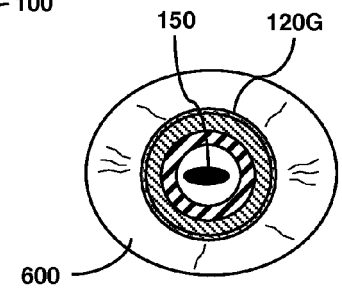
FIG. 6A  FIG. 6B
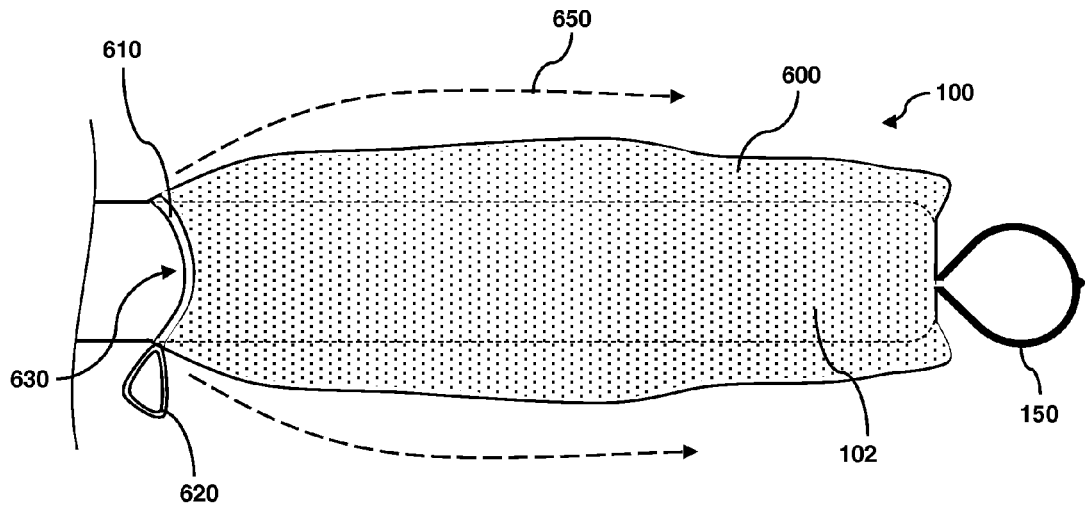
FIG. 6C
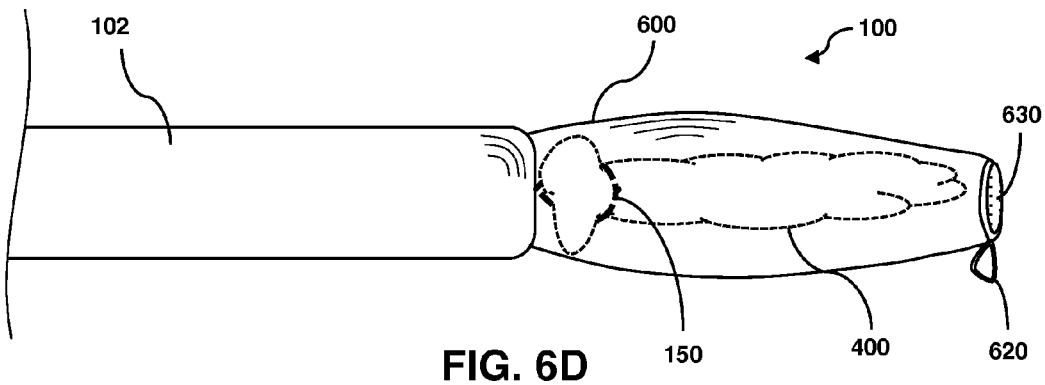
FIG. 6D

FIG. 6E  FIG. 6F

MEDICAL DEVICE FOR SLEEVE GASTRECTOMY SURGERY

BACKGROUND

This section is intended to introduce the reader to aspects of art that may be related to various aspects of the present disclosure described herein, which are described and/or claimed below. This discussion is believed to be helpful in providing the reader with background information to facilitate a better understanding of the various aspects of the present disclosure described herein. Accordingly, it should be understood that these statements are to be read in this light, and not as admissions of prior art.

Laparoscopic gastric sleeve surgery or vertical sleeve gastrectomy (VSG) involves removing or resecting approximately 70%-90% of a patient's stomach and leaving a tube or gastric sleeve. During VSG and other operations involving the esophagus and stomach, there is a need for placement of a bougie, which can be a slender, flexible, and cylindrical instrument for introduction into a tubular organ. The bougie can be placed down via the mouth and across the esophagus and/or stomach or small bowel. The purpose of this device is to act to dilate strictures and/or help delineate or function as a guide for the borders of the stomach and esophagus for resection of the stomach.

Conventional VSG procedures are generally highly invasive and can involve up to five (5) various incisions to successfully perform, which further can require up to six (6) weeks of recovery time, "inpatient" hospital stays, potential complications, and undesirable cosmetic scarring. Therefore, it is desirable for VSG patients to have a minimally invasive procedure that results in less pain, lower risk of complications, faster recovery, and few scars. One recent method of performing a minimally invasive procedure is known as Natural Orifice Transluminal Endoscopic Surgery (NOTES). The NOTES procedure for VSG, or a variation thereof, can include using various natural entrances to the abdominal cavity (i.e. rectum, vagina, etc.) to remove the resected stomach, thereby minimizing incisions. For example, in one study, Mintz et al. (Mintz Y, Horgan S, Savu M K, et al. Hybrid natural orifice translumenal surgery (NOTES) sleeve gastrectomy: a feasibility study using an animal model. Surg Endosc. 2008; 22:1798-802) performed a hybrid NOTES sleeve gastrectomy in a porcine model. In the study, they report their experience utilizing abdominal and rectal entry sites to perform the gastric sleeve procedure. In general, a 5 mm trocar and laparoscope was placed for pneumoperitoneum and visualization, and a 12 mm or 15 mm laparoscope placed transanally through the rectal wall of the model. Further, sutures via the anterior abdominal wall were placed into the stomach to aid retraction and exposure and a stapler was placed through the transrectal trocar to resect the stomach and the resected stomach extracted through transanally through the proctomy.

While advances have been made in achieving minimally invasive VSG procedures, there is still a need to further improve VSG procedures that involve minimal incisions, faster recovery, and less complication. Hence, what is needed is an apparatus and method of performing minimally invasive VSG procedures that reduce the number and size of the incisions, reduce operating costs, reduce the need for expensive surgical equipment, promote faster patient recovery, and further reduce complications associated with VSG surgery.

BRIEF SUMMARY

In one aspect of the present disclosure described herein, a dual-purpose surgical bougie is disclosed for VSG procedures, and other related operations, that can serve the purpose of both operating as a guide or dilator for stapling and resecting a stomach and also extracting securing, containing, and trans-orally extracting the resected stomach, thereby minimizing operating costs, promote faster patient recovery, minimize and reduce the size and number of incisions, and further reduce VSG procedure related complications.

Specifically, in one aspect of the disclosure described herein, a medical device for sleeve gastrectomy surgery is disclosed. Here, the device can include a flexible member or surgical bougie having a distal end and a proximal end, wherein the surgical bougie is further comprised of at least one of rubber, silicone, plastic, and metal. In addition, a securement member can be coupled to the surgical bougie, wherein the securement member extends from the distal end of the flexible member, such that the securement member securely couples to a detached body tissue. Further, the bougie can also include a central channel passage or opening extending from the proximal end to the distal end. Here, the securement member can be a snare loop or forceps. In addition, the securement member can further include an actuator coupled to the proximal end of the surgical bougie. The surgical bougie can be made of uniform silicone and having a diameter ranging from approximately 10.6 mm to approximately 16 mm. Here, the bougie body can be partially or entirely made of silicone, plastic, rubber, metal, or a polymer. Further, a container, bag, or receptacle may also be connected to the surgical bougie.

In another aspect of the disclosure described herein, a medical device for sleeve gastrectomy surgery is disclosed. The device includes a flexible surgical bougie having a body with a distal end and a proximal end, wherein the bougie is further comprised of a uniform rubber, polymer, or silicone material, and the bougie having a diameter ranging from 32 French up to and including 48 French. In addition, the bougie further includes a channel extending from the distal end to the proximal end of the bougie. A securement member comprised of a surgical snare coupled to the bougie, the snare or securement member can further include a flexible cable assembly disposed within a sheath, wherein the sheath is further disposed within the channel of the bougie, a snare loop formed by the flexible cable assembly extending out the distal end of the bougie, an actuator coupled to the proximal end of the surgical bougie and further coupled to the cable assembly, and a fastener for securing the proximal end of the bougie to the actuator. In addition, the actuator can be configured for controlling the cable assembly and the snare loop, such that the snare loop of the bougie couples to and secure a resected stomach, thus retrieving the resected stomach through an opening in a gastric cavity and extracting the resected stomach through an esophagus and oral cavity.

In addition, the surgical bougie can further include a receptacle coupled to the bougie, and wherein the receptacle is for containing the resected stomach, and wherein the receptacle can be comprised of a flexible or elastic bag. The receptacle can be configured inside-out over the exterior body of the bougie. Alternatively, the receptacle may rolled over the bougie or rolled into a bundle. The receptacle may also be deployable or expandable and further include a closure member. The receptacle can be connected or fixed to the distal end of the bougie. Further, the distal end of the bougie can also include a flanged lip, wherein the receptacle can connect to.

In another aspect of the disclosure described herein, a method of using a medical device for sleeve gastrectomy surgery is disclosed. Here, the method can include inserting a flexible member through an oral cavity and an esophagus, wherein the flexible member further includes a securement member at its distal end. The method can further include positioning the flexible member adjacent to a stomach, fastening one side of the stomach adjacent to the flexible member, resecting the stomach near the fastened side, operating the securement member of the flexible member, thereby coupling the flexible member to the resected stomach, and removing the flexible member and the resected stomach through the esophagus wall and oral cavity. Here, the flexible member can be surgical bougie and the securement member can be a snare or a clamp.

The above summary is not intended to describe each and every disclosed embodiment or every implementation of the disclosure. The Description that follows more particularly exemplifies the various illustrative embodiments.

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following detailed description of various embodiments in connection with the accompanying drawings, in which:

FIG. 4A illustrates a side view of a snare assembly and a cross-sectional side view for the non-limiting embodiment of the dual-purpose bougie of the disclosure described herein and an embodiment for a fastening mechanism of a snare actuator to the bougie body.

FIG. 4B illustrates a side view of the snare assembly and a cross-sectional side view for the embodiment of FIG. 4A of the dual-purpose bougie of the disclosure described herein and the fastening mechanism of the snare actuator to the bougie body in an assembled configuration.

FIG. 6A illustrates a cross-sectional side view for the non-limiting embodiment of the dual-purpose bougie of the disclosure described herein having a receptacle attached at one end of the bougie.

FIG. 6B illustrates a front view for the embodiment of FIG. 6A.

FIG. 6C illustrates an elevated side view for the embodiment of FIG. 6A, wherein the receptacle is placed over the bougie.

FIG. 6D illustrates an elevated side view for the embodiment of FIG. 6C, wherein the receptacle is deployed and inverted to contain and secure a resected stomach or body tissue.

FIG. 6E illustrates a cross-sectional side view for the non-limiting embodiment of the dual-purpose bougie of the disclosure described herein having the receptacle secured at one end of the bougie and having a flanged end.

FIG. 6F illustrates a front view for the embodiment of FIG. 6E.

DETAILED DESCRIPTION

In the Brief Summary of the present disclosure above and in the Detailed Description of the Disclosure described herein, and the claims below, and in the accompanying drawings, reference is made to particular features (including method steps) of the disclosure described herein. It is to be understood that the disclosure of the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein, and in the disclosure described herein generally.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

Figure 1A:
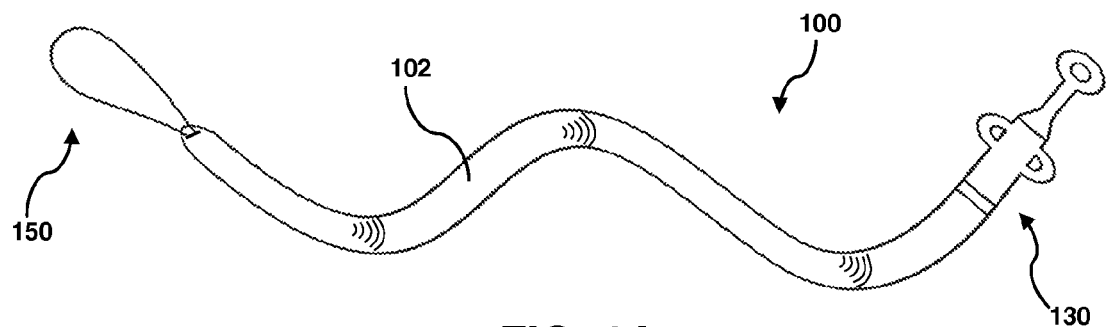
FIG. 1A illustrates a top view for one non-limiting embodiment of a dual-purpose bougie of the disclosure described herein having a snare assembly.
Figure 1B:
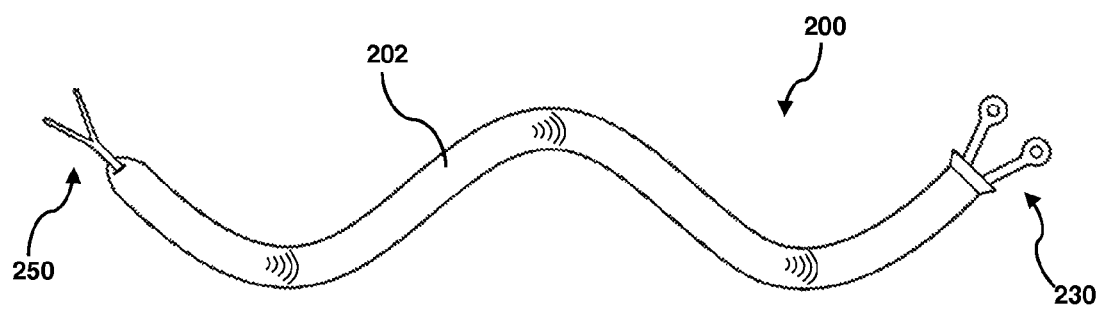
FIG. 1B illustrates a top view for another non-limiting embodiment of the dual-purpose bougie of the disclosure described herein having a forcep or clamp assembly.

FIG. 1A illustrates one non-limiting embodiment for a dual-purpose surgical bougie 100 of the disclosure described herein. In particular, the bougie 100 having a slender, flexible or semi-rigid, and tubular cylindrical body 102. Bougie 100 can further include a snare assembly 130 having a sliding or rotational snare actuator handle secured at a proximal end of body 102 for operating and controlling a deployable snare loop 150 extending from the distal end of body 102. FIG. 1B illustrates another non-limiting embodiment for a surgical bougie 200 of the disclosure described herein. Here, bougie 200 can also have a slender, flexible or semi-rigid, and tubular cylindrical body 202, and clamp, jaw, scissor, stapler, and/or forceps assembly 230 having an actuator secured at a proximal end of body 202 for operating and controlling a deployable clamp, jaw, scissor, stapler, and/or forceps 250 extending from the distal end of the body 202. However, it is contemplated within the scope of the disclosure described herein that other securement members may also be used for the bougie.

Figure 2A:
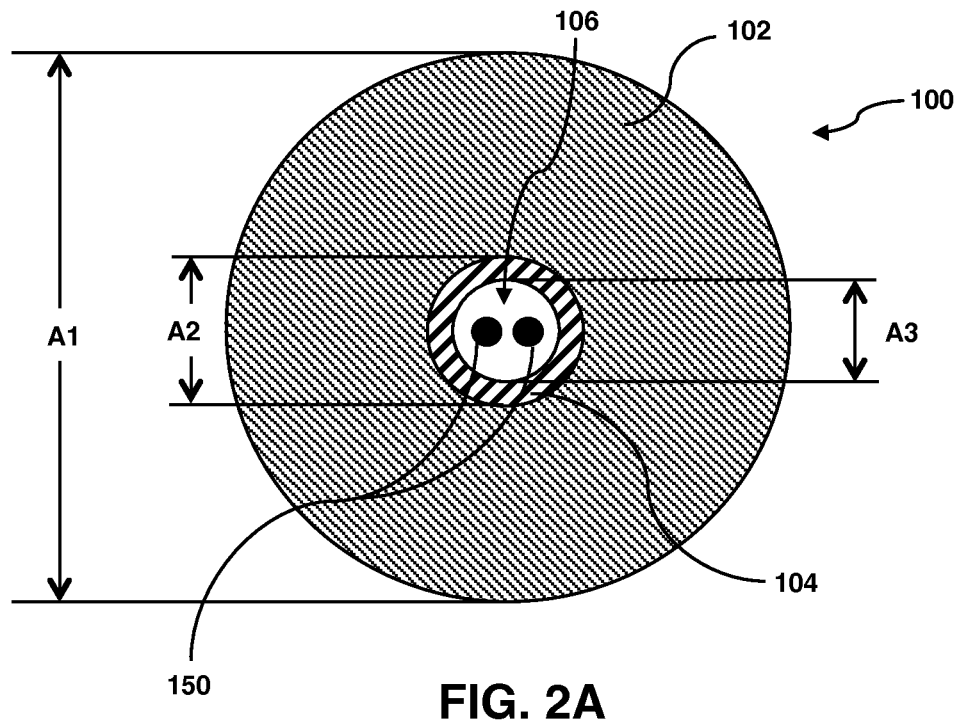
FIG. 2A illustrates a cross-sectional front view for the non-limiting embodiment of the dual-purpose bougie of the disclosure described herein.
Figure 2B:
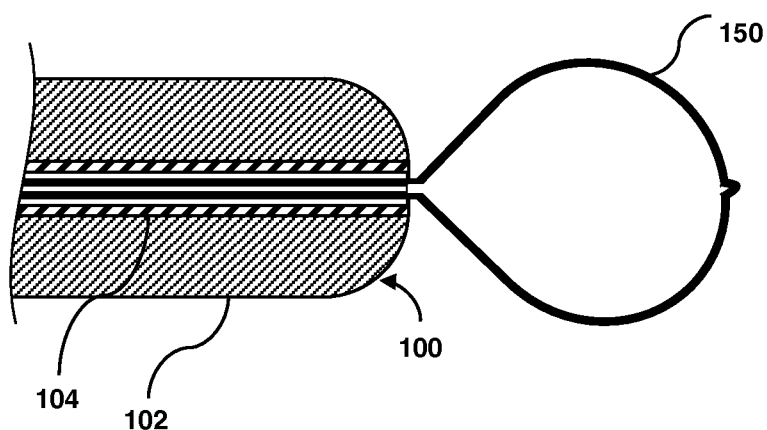
FIG. 2B illustrates a cross-sectional side view for the non-limiting embodiment of the dual-purpose bougie of the disclosure described herein having a blunt end.
Figure 2C:
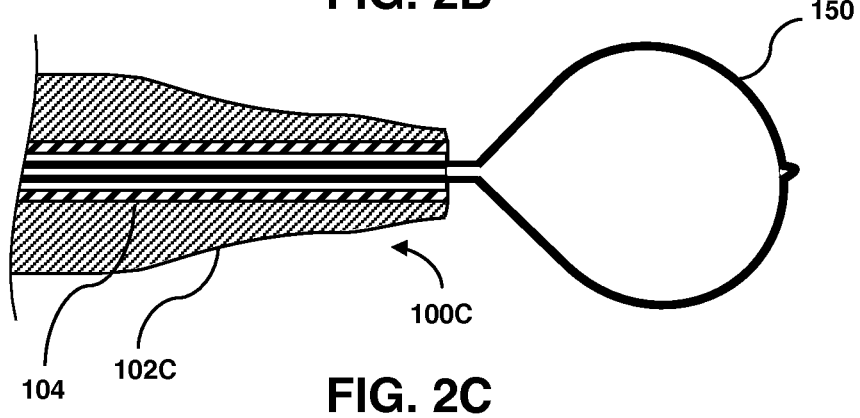
FIG. 2C illustrates a cross-sectional side view for a non-limiting embodiment of the dual-purpose bougie of the disclosure described herein having a tapered end.

FIG. 2A illustrates the bougie 100 of the disclosure described herein. Here, bougie 100 can include the cylindrical body made of uniform flexible rubber, silicone, plastic, or metal material. The diameter A1 of body 102 can range from 32 French (approximately 10.6 mm) up to and including 48 French (approximately 16 mm). Alternatively, the bougie can be sized from 10 French up to and including 100 French and having any length such as from 6 inches up to and including 60 inches. Also, the bougie may telescoping, foldable, or retractable in order to alter its size, form, configuration, or dimensions, whether within or outside of the body. In addition, body 102 can include a channel or passageway 106 extending the entire length of the bougie, wherein the channel can have a diameter A2 ranging from 0.1 mm up to and including 16 mm. In addition, there may be a lumen, shaft, or sheath 104 disposed within channel 106, wherein the sheath can have a diameter A3 ranging from 0.1 mm up to and including 16 mm. Here, sheath 104 can serve the purpose of enclosing the snare cable assembly 150 disposed within the sheath 104 and channel 106 and allowing fluid and non-restricted operation of the cable assembly 150 within body 102. However, it is contemplated within the scope of the disclosure described here that the body 102 may also include two or more sheaths, or two or more snare cable assemblies disposed within independent offset channels, such as one snare per channel. Alternatively, the two or more snare cable assemblies may all be disposed within one channel. FIG. 2B illustrates the bougie 100 of the disclosure described herein shown having the body 102 with a blunt distal end, and FIG. 2C illustrating a bougie 100C having a body 102C with a tapered or pointed distal end. However, it is contemplated within the scope of the disclosure described herein that the bougie body may have any type of configuration, dimension, or shape, either at its proximal, middle, or distal ends, including but not limited to blunt, tapered, rounded corners, triangular, oval, spear, cone or funnel, inverted cone or funnel, or the like.

Figures 3A, 3B:
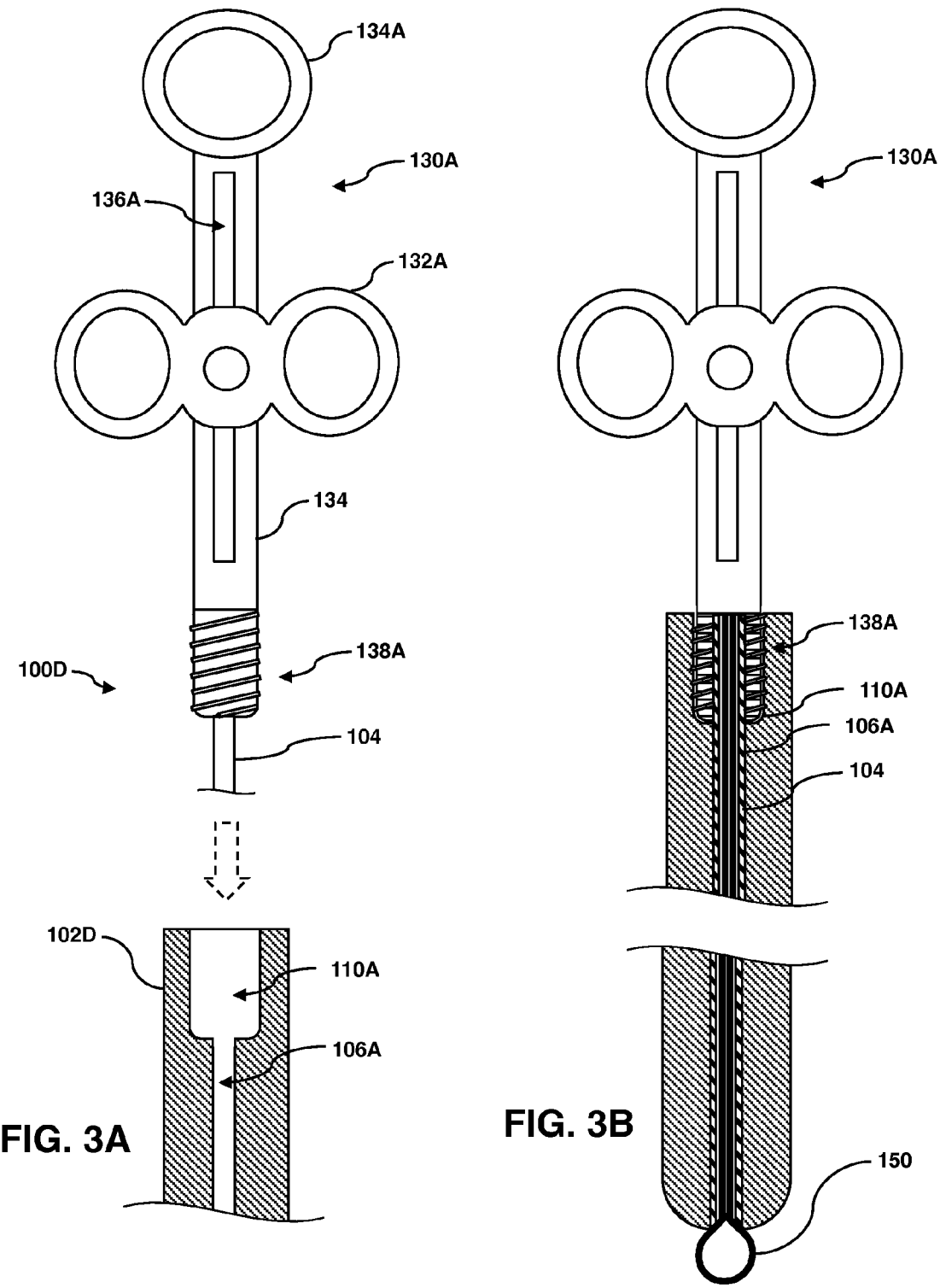
FIG. 3A illustrates a side view of a snare assembly and a cross-sectional side view for one non-limiting embodiment of the dual-purpose bougie of the disclosure described herein and a fastening mechanism for a snare actuator to the bougie body.
FIG. 3B illustrates a side view of a snare assembly and a cross-sectional side view for the embodiment of FIG. 3A of the dual-purpose bougie of the disclosure described herein and the fastening mechanism of the snare actuator to the bougie body in an assembled configuration.

FIGS. 3A-3B illustrate one embodiment for a bougie 100D and securing and coupling a snare assembly 130A and its actuator 134 to a proximal end of bougie body 102D. Here, snare assembly 130A can include any type of manual or automatic/powered actuator 134 having dual-loop dual-finger operated component 132A slidably or rotationally coupled to a second single-loop single finger held component 134A, wherein component 132A slides back and forth within an opening or track 136A to deploy the snare cable and corresponding snare loop 150 and control the deployability, expandability, rotation, position, size, grip, force, pressure, self-orienting, manipulation, and maneuverability of snare loop 150, among other operational features. For example, the snare assembly 130A may also include one or more swivel components for deploying the snare loop cable 150. However, it is contemplated within the scope of the disclosure herein, that any other re-usable or disposable surgical snare assembly known in the art may also be assembled to, retro-fitted to, attached to, integrated with, and used with the bougie of the disclosure described herein.

Still referring to FIG. 3A-3B, the snare actuator handle 134 may have a threaded male distal end 138A configured to engage and securely couple within a female threaded opening 110A. In addition, channel 106A can further receive the sheath 104 (for housing the cable snare 150) therein. For example, in one embodiment for a method of manufacture or assembly, an existing snare assembly 130A may be retro-fitted to an existing bougie 100D of the disclosure described herein. In such an embodiment, a threaded tubular part, such as 138A, can be slid over sheath 104 (such as from the sheath's distal end) and fastened to the lower end body of actuator 134, such as via adhesives, screws, bolts, or related fasteners. In such an embodiment, area 110A and channel 106A may be cut, shaved, stamped, molded, or drilled out. Once part 138A is secured to the actuator 134, then part 138A, along with actuator 134, can then be securely coupled to the proximal end of the bougie body, such as via threaded engagement (as shown), screws, bolts, adhesives, or related fasteners. Alternatively, the bougie body may be a custom size and configuration so that the snare assembly 130A may be secured to the bougie body 102D at the time of manufacture, or wherein assembly 130A and body 102E are one unitary piece.

FIGS. 4A-4B illustrates the bougie 100 and securing and coupling the snare assembly 130 and its actuator to a proximal end of bougie body 102. Here, snare assembly 130 can include any type of manual or automatic/powered actuator having a dual-loop dual-finger operated component slidably coupled to a second single-loop single finger held component, wherein the two finger component slides back and forth within an opening or track to deploy the snare cable and corresponding snare loop 150 and control the size, grip, pressure, and maneuverability of snare loop, among other operational features. However, it is contemplated within the scope of the disclosure herein, that any other surgical snare assembly known in the art may also be assembled to, attached to, and within the bougie of the disclosure described herein. For example, the snare assembly 130 may also include one or more swivel components for deploying the snare loop cable 150. However, it is contemplated within the scope of the disclosure herein, that any other re-usable or disposable surgical snare assembly known in the art may also be assembled to, retro-fitted to, attached to, integrated with, and used with the bougie of the disclosure described herein.

Still referring to FIG. 4A-4B, the snare actuator may have a threaded female distal end or cap 138 configured to engage and securely couple to a threaded male end 110 of the bougie body. In addition, channel 106 can further receive the sheath 104 (for housing the cable snare 150) therein. For example, in one embodiment for a method of manufacture or assembly, an existing snare assembly 130 may be retro-fitted to the existing bougie 100 of the disclosure described herein. In such an embodiment, cap 138 (have a central opening) can be slid over sheath 104 (such as from its distal end) and fastened to the lower end body of the actuator, such as via adhesives, screws, bolts, or related fasteners. In such an embodiment, end 110 may be pre-threaded, molded, and cut, and channel 106 may be cut, shaved, stamped, molded, or drilled out. Once cap 138 is secured to the actuator, then part 138, along with the actuator, can then be securely coupled to the proximal end of the bougie body, such as via threaded engagement (as shown), screws, bolts, adhesives, or related fasteners. Alternatively, the bougie body may be a custom size and configuration that the snare assembly 130 may be secured to the bougie body 102 at the time of manufacture, or wherein assembly 130 and body 102 are one unitary piece.

Figure 5A:
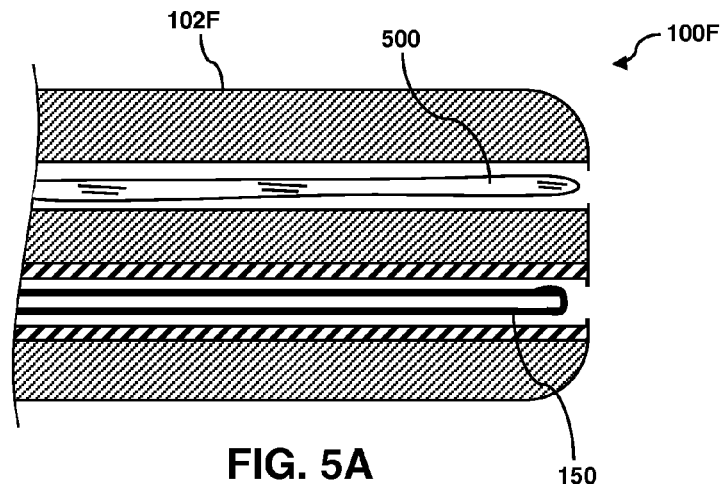
FIG. 5A-5B illustrate a cross-sectional side views for one non-limiting embodiment of the dual-purpose bougie of the disclosure described herein having a deployable receptacle for containing a resected stomach or body tissue.
Figure 5B:
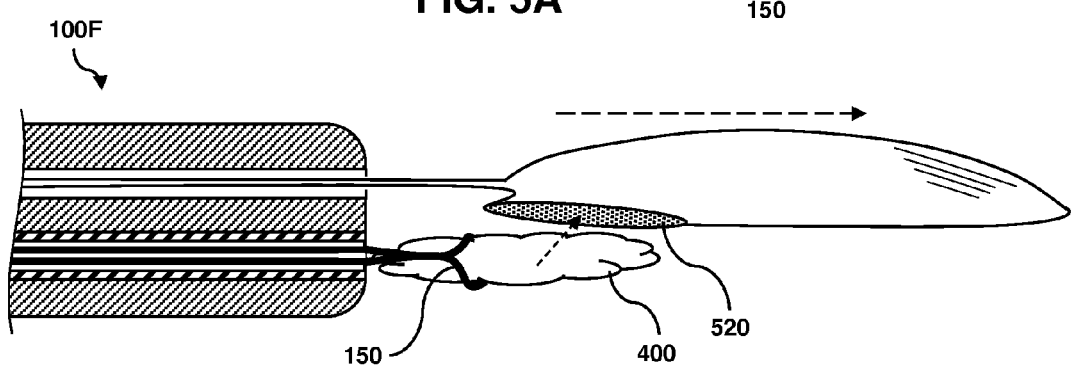
Figure 5C:
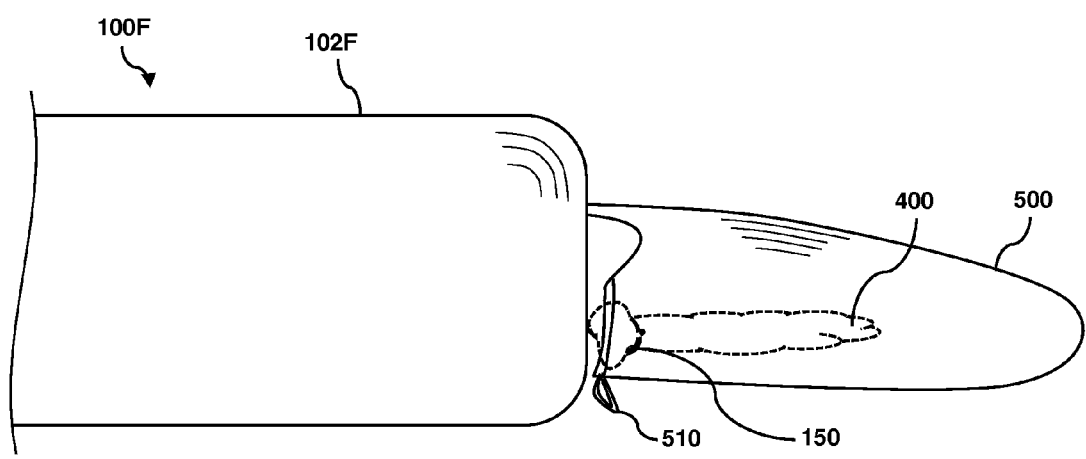
FIG. 5C illustrates an elevated side view of for the embodiment of FIG. 5A-5B, wherein in one non-limiting embodiment the resected stomach contained and secured within the receptacle.

FIG. 5A-5C illustrate one embodiment for a bougie and receptacle assembly for the disclosure described herein. Here, bougie 100F having bougie body 102F is shown having dual channels or passages, one for housing deployable cable snare loop 150 and another for housing deployable receptacle 500. Here, receptacle 500 may be any elongated flexible, elastic, foldable, and expandable vessel, cover, bag, or container for containing or covering body tissue, such as a resected stomach 400. In particular, FIG. 5A illustrates receptacle 500 in its un-expanded, folded, un-deployed, and collapsed configuration within a first channel of body 102F, and also cable snare loop 150 in its un-deployed, folded, and collapsed configuration within a second channel. FIG. 5B illustrates receptacle 500 being deployed and expanded and having an opening 520 for receiving resected stomach 400 secured with and placed within receptacle 500 via deployed snare loop 150, or in combination with one or more surgical tools. FIG. 5C illustrates resected stomach 400 contained within receptacle 500. In addition, receptacle 500 may also include a securement member, such as an elastic band or drawstring 510 around opening 520 for closing the opening and further securing the contents therein.

FIG. 6A-6D illustrate the embodiment for the bougie and receptacle assembly of the disclosure described herein having a receptacle. Here, bougie 100 having body 102 is shown having receptacle 600 securely fixed or attached to the distal end of body 102 and snare cable assembly 150 disposed within a central channel. Here, receptacle 600 may be any elongated flexible, elastic, foldable, and expandable vessel, cover, bag, shrink wrap, or container for containing, covering, and retrieving body tissue, such as a resected stomach 400. In this embodiment, retrieval receptacle 600 can be fixed or attached to a circular opening, wedge, cut-out 120G, wherein one end of the receptacle 600 is secured within cut-out 120G or at distal end area 120G, such as via adhesives, ring, bolt, clamp, or snap-fit. In particular, FIG. 6A-6C illustrate receptacle 600 in its un-deployed configuration, wherein receptacle 600 is initially pulled over the exterior of body 102. In addition, receptacle 600 may also be secured to the body via elastic band 610 or drawstring 620, which may or mat not include a tab. Alternatively, one end of receptacle 600 may be detached, floating, or hovering over the exterior bougie body 102. In other embodiments, receptacle 600 may be rolled up in its un-deployed configuration. FIG. 6D illustrates receptacle 600 in its deployed configuration. In particular, referring back FIG. 6C, the free end of receptacle 600 may be rolled or pulled back via the direction of arrows 650 using one or more surgical tools or forceps. More specifically, receptacle 600 is pulled back from its open end 630 wherein open end 630 of receptacle encloses or wraps over stomach 400 until receptacle 600 is at least partially, entirely, or substantially inverted or inside-out, thereby partially, entirely, or substantially containing resected stomach 400 and the snare loop 150 therein, wherein loop 150 secures stomach 400 (FIG. 6D). In addition, band, tab, or drawstring 610 and 620 may be used to close or secure opening end 630. One advantage of the receptacle is that it allows containment of the resected stomach or body tissue and a non-restrictive smooth extraction of the resected through the esophagus and oral cavity and further preventing any potential inflammation, infection, wound, or damage to surrounding organs, tissue, esophagus, or oral cavity. For example, in some embodiments, the receptacle may be of any thickness and elasticity, and may also be coated with any coating or lubricating substance for a smooth and non-stick surface.

Figure 6G:
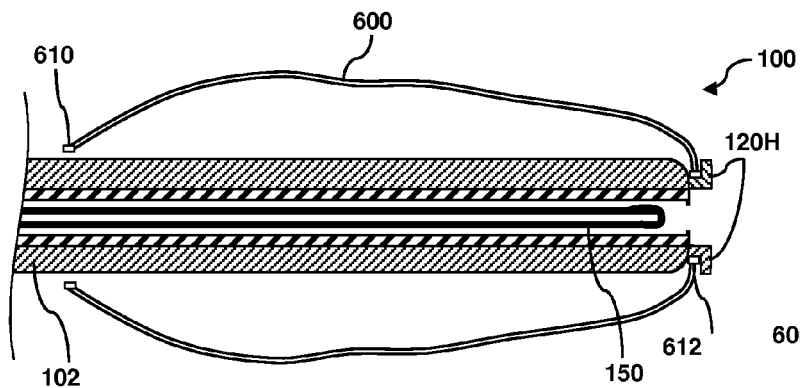
FIG. 6G illustrates a side view for the embodiment of FIG. 6E, wherein the receptacle is placed over the bougie.
Figure 6G:
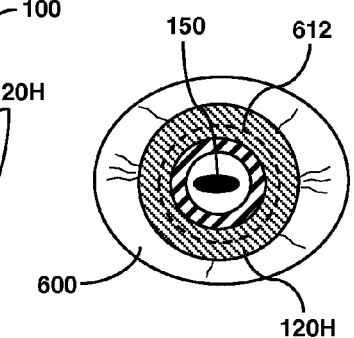
Figure 6G:
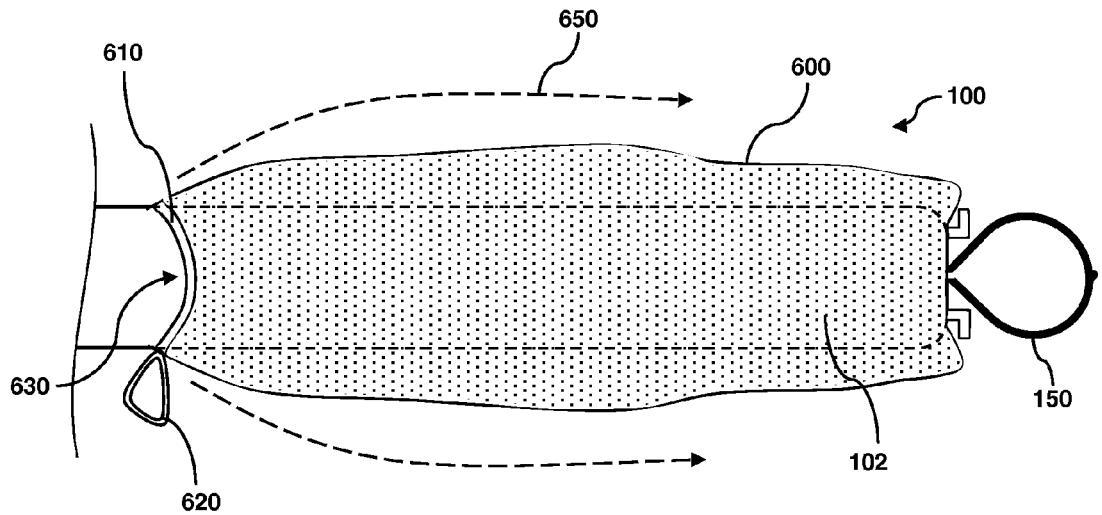
Figure 6H:
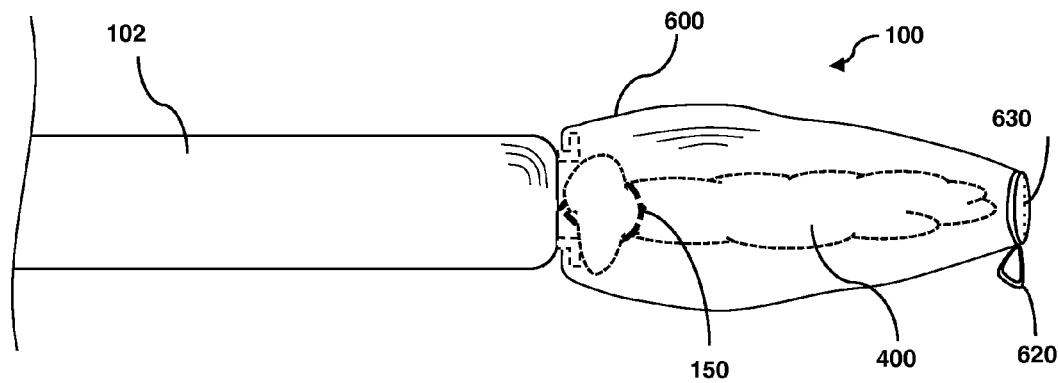
FIG. 6H illustrates a side view for the embodiment of FIG. 6G, wherein the receptacle is deployed and inverted to contain and secure the resected stomach or body tissue.

FIG. 6E-6H illustrate the embodiment for the bougie and receptacle assembly of the disclosure described herein having a flanged end. Here, bougie 100 having body 102 is shown having receptacle 600 securely fixed or attached to the distal end of body 102 and snare cable assembly 150 disposed within a central channel. Here, receptacle 600 may be any elongated flexible, elastic, foldable, and expandable vessel, cover, bag, shrink wrap, or container for retrieving, containing, covering body tissue, such as a resected stomach 400. In this embodiment, retrieval receptacle 600 can be fixed or attached to a circular flanged or lip groove opening 120H of body 102, wherein one end of the receptacle 600 may include an elastic or tapered band end 612 for being placed around and within the circular opening groove of flange 120H, and secured or fixed to flange 120H and body 102 via adhesives, clamp, elastic fit, or snap-fit. In particular, FIG. 6E-6G illustrate receptacle 600 in its un-deployed configuration, wherein receptacle 600 is initially pulled over the exterior of body 102. In addition, receptacle 600 may also be secured to the body via elastic band 610 or drawstring 620, which may or mat not include a tab. Alternatively, one end of receptacle 600 may be detached, floating, or hovering over the exterior bougie body 102, as shown in FIG. 6E. In other embodiments, receptacle 600 may be rolled up its un-deployed configuration. FIG. 6H illustrates receptacle 600 in its deployed configuration. In particular, referring back FIG. 6G, the free end of receptacle 600 may be rolled or pulled back via the direction of arrows 650 using one or more surgical tools or forceps, or via tab 620. More specifically, receptacle 600 is pulled back wherein open end 630 of receptacle encloses or wraps over stomach 400 until receptacle 600 is at least partially, entirely, or substantially inverted or inside-out, thereby partially, entirely, or substantially containing resected stomach 400 and the snare loop 150 therein, wherein loop 150 secures stomach 400 (FIG. 6H). In addition, band, tab, or drawstring 610 and 620 may be used to close or secure opening end 630. One advantage of the receptacle is that it allows containment of the resected stomach or body tissue and a non-restrictive smooth extraction of the resected through the esophagus and oral cavity further preventing any potential inflammation, infection, wound, or damage to surrounding organs, tissue, esophagus, or oral cavity. For example, in some embodiments, the receptacle may be of any thickness and elasticity, and may also be coated with any coating or lubricant material for a smooth and non-stick surface.

Figure 6I:
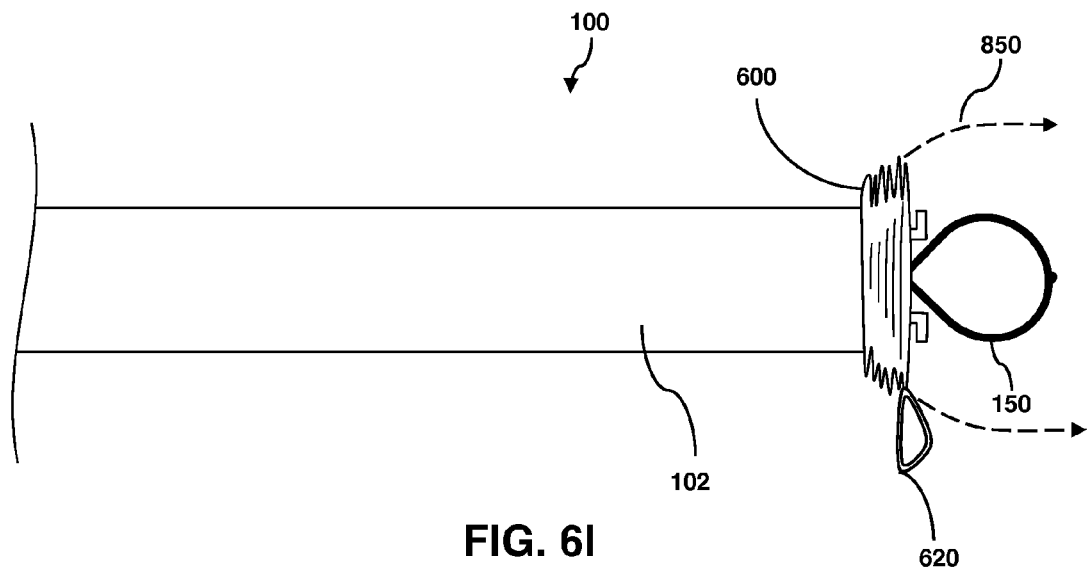
FIG. 6I illustrates a side view for the non-limiting embodiment of the dual-purpose bougie of the disclosure described herein wherein the receptacle is shown in a rolled up configuration and attached at the distal end of the bougie.
Figure 6J:
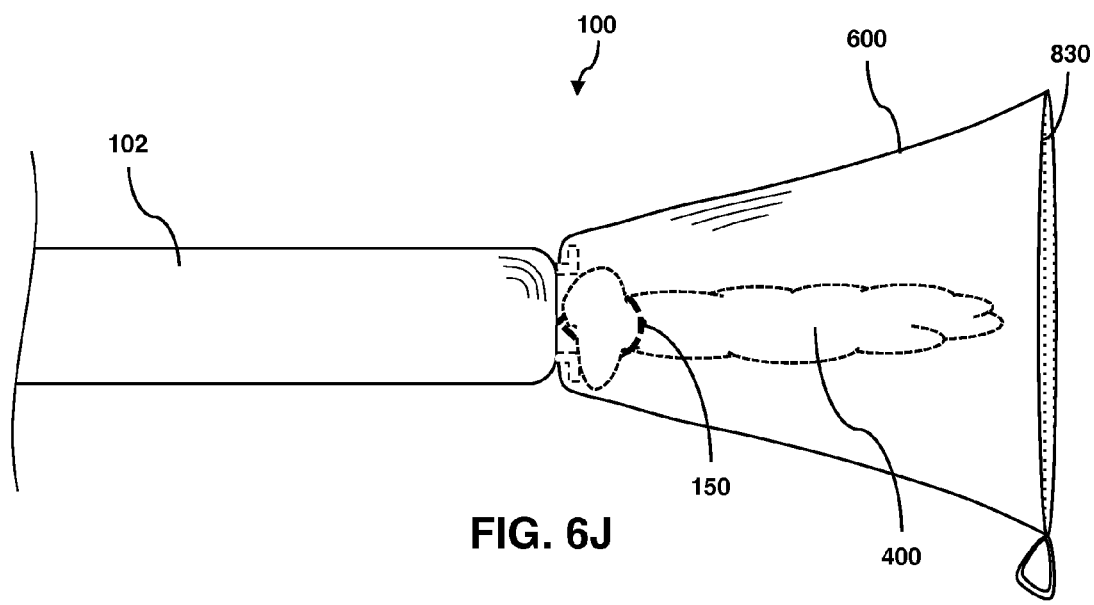
FIG. 6J illustrates a side view for the embodiment of FIG. 6I, wherein the receptacle is deployed and shown in a rolled out configuration to contain and cover a resected stomach or body tissue.

FIG. 6I-6J illustrate the embodiment for the bougie and receptacle assembly of the disclosure described herein. Here, bougie 100 having body 102 is shown having receptacle 600 securely fixed or attached to the distal end of body 102 and snare cable assembly 150 disposed within a central channel. Here, receptacle 600 may be any elongated flexible, elastic, foldable, and expandable vessel, cover, bag, shrink wrap, or container for retrieving, containing, covering body tissue, such as a resected stomach 400. In this embodiment, retrieval receptacle 800 can be fixed or attached to a circular flanged or lip groove opening body 102 or coupled, attached, or fixed at near the distal end of body 102, wherein one end of the receptacle 600 may be secured to body 102 via adhesives. Alternatively, receptacle 600 may be secured to the body via elastic or expandable fitment. Here, receptacle 600 is shown either rolled up in a bundle, collapsed, or folded configuration prior to deployment. FIG. 6J illustrate receptacle 600 in its un-deployed configuration, wherein receptacle 600 is initially pulled and unrolled. In particular, the free end of receptacle 600 may be un-rolled, rolled back, expanded, or pulled back via the direction of arrows 850 using one or more surgical tools or forceps, or via tab 620. More specifically, open end 830 of receptacle 800 is rolled over the stomach 400 until receptacle 600 partially, entirely, or substantially contains resected stomach 400 and the snare loop 150 therein, wherein loop 150 secures stomach 400 (FIG. 6H). In addition, band, tab, or drawstring 620 may be used to close or secure open end 830. One advantage of the receptacle is that it allows containment of the resected stomach or body tissue and a non-restrictive smooth extraction of the resected through the esophagus and oral cavity further preventing any potential inflammation, infection, wound, or damage to surrounding organs, tissue, esophagus, or oral cavity. For example, in some embodiments, the receptacle may be of any thickness and elasticity, and may also be coated with any coating or lubricant material for a smooth and non-stick surface.

Figure 7A:
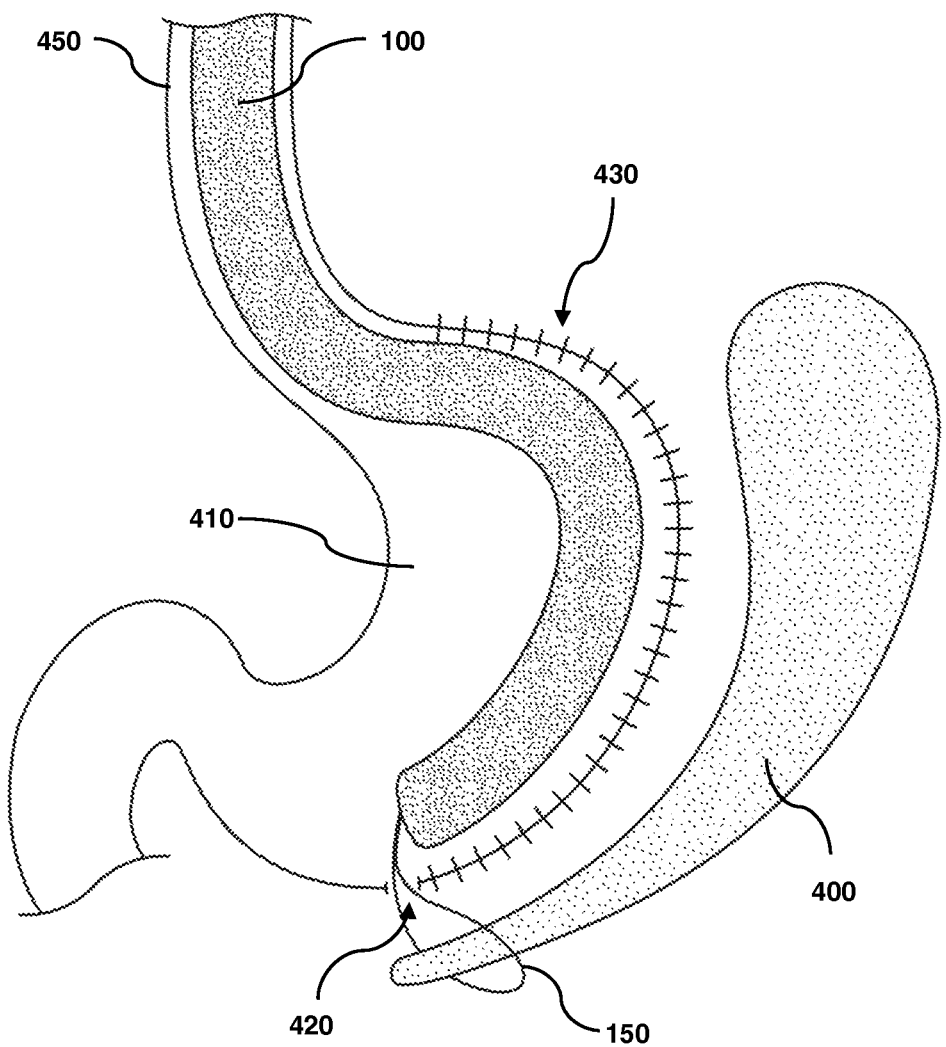
FIG. 7A illustrates a partial cross-sectional environmental view for one non-limiting embodiment method of a VSG procedure with a top view of the dual-purpose bougie of the disclosure described herein being used to secure a resected stomach.
Figure 7B:
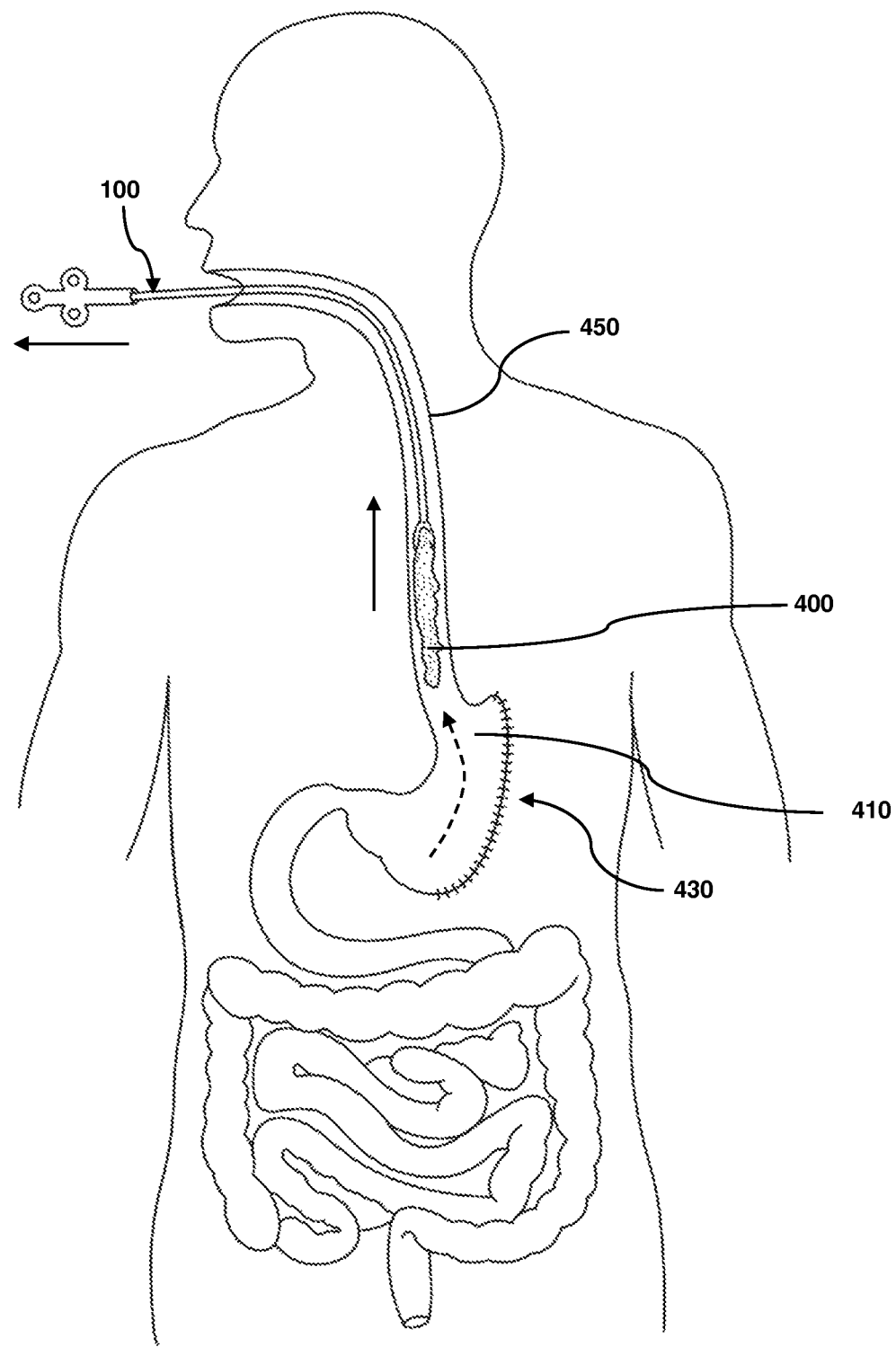
FIG. 7B illustrates a partial cross-sectional environmental view for one non-limiting embodiment method of a VSG procedure with a top view of the dual-purpose bougie of the disclosure described herein being used to extract the resected stomach trans orally.

FIG. 7A-7B illustrate one embodiment for a method of at performing, at least in part, a VSG procedure using the bougie of the disclosure described herein for the aforementioned embodiments. Further, the VSG procedure and use of the bougie of the disclosure described herein may also be considered as a variation of a Natural Orifice Trans-endoluminal Esophageal Surgery (NOTES) procedure, or a partial NOTES procedure on a human. In particular, during a VSG procedure, the bougie 100 can be inserted via a patient's oral cavity and esophagus 450 into a stomach and gastric cavity. Here, a first use or first purpose of the bougie is positioning the bougie within the stomach/gastric cavity and using it for sizing and calibrating the stomach and/or used as a guide for stapling and cutting the stomach along staple line 430, thereby leaving a gastric sleeve stomach 410, wherein stomach 400 is entirely detached or resected via the staple line 430. The second use of the bougie is for deploying the securement member or snare loop 150 and coupling the snare loop and bougie to a lower end region of resected stomach 400 and retrieving or extracting the stomach via the bougie and snare loop through an opening 420 within the gastric cavity. More specifically, an incision opening 420 may be made either prior to stapling or after stapling at the bottom floor or lower region of the gastric stomach cavity, thereby allowing snare loop 150, and bougie 100, to slide there through and to secure resected stomach 400 and to retrieve and extract stomach 400 through incision opening 420. In addition, at anytime the aforementioned receptacle of the disclosure described herein may also be deployed to contain the extracted stomach 400. As shown in the direction of arrows in FIG. 7B, the resected stomach 400 is pulled, retrieved, and extracted via the bougie of the disclosure described herein through the esophagus 450 and out of the oral cavity of a patient. After extraction of the stomach 400 through the oral cavity, incision opening 420 can then be sutured and closed.

It is contemplated within the scope of the disclosure herein that the bougie, including its receptacle, securement members, or actuator and snare cable assembly, may also be disposable or re-usable. In other embodiments, the bougie may also be mechanically or automatically controlled via a locally and electrically powered connection or controlled remotely via one or more networked or wireless computing devices. In other embodiments, the bougie may also be a dilator, include a dilating member, or include endoscopic, camera, and lighting components. In addition, the size of the bougie used may also depend on the weight, size, diet, age, exercise habits, condition of the patient or the size of the resected stomach to be extracted, or gastric sleeve size. It is further contemplated within the scope of the disclosure herein that other surgical procedures for VSG, or the like, may also be performed using the bougie of the disclosure described herein, including but not limited to human or animal bariatric surgery, orthopedic, spine, bypass surgery, gastric bypass, gastric band or Lap-Band®, cosmetic, laparoscopy, open body, resection, reconnection, ligation, arthrodesis, excision surgery (-ectomy), cutting procedure (-otomy), minimally invasive (-oscopy), endoscopic, stoma (-ostomy), or any ectomy based, reconstructive (-oplasty), and congenital defects surgery (-rraphy), among others.

It is further contemplated within the scope of the disclosure described herein that the bougie, bougie body, receptacle, sheath, securement members, snare cable, and snare assembly may also be made of polymers, plastics, silicones, rubbers, metals, metal alloys, metal-polymer composites, anti-bacterial, anti-microbial, bio-compatible, latex-free, non-sterile, sterile materials, and the like. Some examples of suitable polymers may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, polyethylene (PE), Marlex high-density polyethylene, Marlex low-density polyethylene, linear low density polyethylene (for example, REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and some examples of suitable metals and metal alloys including stainless steel, such as 304V, 304 L, and 316 L stainless steel; nickel-titanium alloy such as linear-elastic or super-elastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material. In addition, the bougie, bougie body, receptacle, sheath, and securement members can also be blended with a liquid crystal polymer (LCP). For example, the mixture can contain up to about 5% LCP. By employing selection of materials and processing techniques, thermoplastic, solvent soluble, and thermosetting variants of these and other materials can be employed to achieve the desired results.

Having thus described the several embodiments of the present disclosure described herein, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes can be made with respect to various elements described herein without exceeding the scope of the invention. Although the present disclosure described herein has been described in considerable detail with reference to certain preferred versions or embodiments thereof, other versions and embodiments are possible. Therefore, the spirit and scope of the appended claims should not be limited to the description of the embodiments contained herein.

What is claimed is:

1. A medical device for sleeve gastrectomy surgery, the device comprising:
   an esophageal bougie dilator having a body with a blunt distal end and a proximal end, wherein the blunt distal end comprises a curved region;
   one end of a receptacle fixed to the curved region of the blunt distal end of the esophageal bougie dilator and another opposing end of the receptacle unsecured to the esophageal bougie dilator, wherein the receptacle is further disposed inside-out over the exterior of the esophageal bougie dilator;
   an actuator coupled to the proximal end of the esophageal bougie dilator;
   a securement member coupled to the actuator and disposed within the esophageal bougie dilator; and
   wherein the securement member is configured to extend from the blunt distal end of the esophageal bougie dilator, so that the securement member securely couples to a detached body tissue.

2. The medical device of claim 1, wherein the esophageal bougie dilator further comprises a central channel extending from the proximal end to the distal end.

3. The medical device of claim 2, wherein the securement member is comprised of a snare loop.

4. The medical device of claim 1, wherein the distal end further comprises a flanged end.

5. The medical device of claim 1, wherein the actuator is coupled to the proximal end of the esophageal bougie dilator via a threaded engagement.

6. The medical device of claim 1, wherein the esophageal bougie dilator is made of uniform silicone and having a diameter ranging from approximately 10.6 mm to approximately 16 mm.

7. A medical device for sleeve gastrectomy surgery, the device comprising:
   a flexible semi-rigid surgical bougie dilator having a body with a curved distal end and a proximal end, wherein the bougie is further comprised of a uniform rubber, polymer, or silicone material, and wherein the bougie dilator further comprises a diameter ranging from 32 French up to and including 48 French;
   a first end of a receptacle secured to the curved distal end of the bougie dilator and a second end of the receptacle unsecured relative to the bougie dilator;
   a channel extending from the distal end to the proximal end of the bougie dilator;
   a securement member comprised of a surgical snare coupled to the bougie, the surgical snare further comprising:
      a flexible cable assembly disposed within a sheath, wherein the sheath is further disposed within the channel of the bougie dilator;
      a snare loop formed by the flexible cable assembly extending out the distal end of the bougie dilator;
      a handle actuator coupled to the proximal end of the surgical bougie dilator and further coupled to the cable assembly;
      a fastener configured to secure the proximal end of the bougie to the actuator; and
   wherein the actuator is configured to control the cable assembly and the snare loop, so that the snare loop of the bougie dilator couples to and secures a resected stomach, thereby retrieving the resected stomach through an opening in a gastric cavity and extracting the resected stomach through an esophagus and oral cavity.

8. The medical device of claim 7, wherein the receptacle is configured to contain the resected stomach.

9. The medical device of claim 8, wherein the receptacle is comprised of a flexible or elastic bag.

10. The medical device of claim 8, wherein the receptacle is configured inside-out over the exterior body of the bougie.

11. The medical device of claim 8, wherein the receptacle is rolled over the bougie.

12. The medical device of claim 8, wherein the receptacle further comprises a closure member.

13. The medical device of claim 8, wherein the receptacle is deployable.

14. The medical device of claim 7, wherein the distal end of the bougie further comprises a flanged lip.

15. A medical device for sleeve gastrectomy surgery, the device comprising:
   a surgical bougie dilator having a body with a distal tip end with a curved region and a proximal end, wherein the bougie dilator comprises a diameter ranging from 10 French up to and including 100 French;
   a receptacle, wherein one end of the receptacle is fixed to the curved region of the bougie dilator and another opposing end of the receptacle unsecured to the bougie dilator;
   an actuator coupled to the proximal end of the surgical bougie dilator;
   a securement member coupled to the actuator and disposed within the surgical bougie dilator; and
   wherein the securement member is configured to extend from the distal end of the surgical bougie dilator thereby securing a detached body tissue.

16. The medical device of claim 15, wherein the securement member is comprised of a snare.

* * * * *